(12) United States Patent
Hashmi et al.

(10) Patent No.: US 9,801,670 B2
(45) Date of Patent: Oct. 31, 2017

(54) LOCKING FIRST METACARPAL PLATE

(71) Applicant: DePuy Synthes Products, Inc., Raynham, MA (US)

(72) Inventors: Adam Hashmi, West Chester, PA (US); Lynn Kelly, West Chester, PA (US); Daneen Touhalisky, West Chester, PA (US); James Guthlein, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 618 days.

(21) Appl. No.: 14/320,542

(22) Filed: Jun. 30, 2014

(65) Prior Publication Data
US 2015/0374424 A1    Dec. 31, 2015

(51) Int. Cl.
*A61B 17/88* (2006.01)
*A61B 17/80* (2006.01)

(52) U.S. Cl.
CPC .............................. *A61B 17/8061* (2013.01)

(58) Field of Classification Search
None
See application file for complete search history.

(56) References Cited

U.S. PATENT DOCUMENTS

| 7,731,718 B2 | 6/2010 | Schwammberger et al. |
| 2007/0239163 A1 | 10/2007 | Strnad et al. |
| 2011/0264149 A1* | 10/2011 | Pappalardo ........ A61B 17/8019 606/286 |

FOREIGN PATENT DOCUMENTS

| EP | 1707227 | 10/2006 |
| EP | 2623059 | 8/2013 |
| WO | 2013/036362 | 3/2013 |

* cited by examiner

*Primary Examiner* — Sameh Boles
(74) *Attorney, Agent, or Firm* — Fay Kaplun & Marcin, LLP

(57) ABSTRACT

A bone plate sized and shaped for fixation to a phalangeal bone includes a head extending from a first end to a second end and having first, second third and fourth fixation element holes extending therethrough and arranged in a diamond configuration on the head, an outer wall of the head having a diamond shape corresponding to the diamond configuration, a bone contacting surface of the head being contoured to conform to the anatomy of a dorsal surface of a first metacarpal, the contour being curved to be seated over a protuberance at a head of the first metacarpal and a shaft extending from the head, the shaft including an elongated fixation element hole elongated in a direction parallel to a longitudinal axis of the bone plate.

9 Claims, 1 Drawing Sheet

LOCKING FIRST METACARPAL PLATE

FIELD OF THE INVENTION

The present invention generally relates to bone plates for the fixation of fractures of the hand and methods of coupling these plates to bone.

BACKGROUND

Many current systems and methods for the fixation of fractures are limited in the placement and orientation of plates over the bone. For example, current systems for the fixation of fractures of the first metacarpals are often confined to limited placements dictated heavily by the construction of the plate and often are not suitable for placement in an optimum location for the fracture.

SUMMARY OF THE INVENTION

The present invention is directed to a bone plate sized and shaped for fixation to a phalangeal bone, comprising a head extending from a first end to a second end and having first, second third and fourth fixation element holes extending therethrough and arranged in a diamond configuration on the head, an outer wall of the head having a diamond shape corresponding to the diamond configuration, a bone contacting surface of the head being contoured to conform to the anatomy of a dorsal surface of a first metacarpal, the contour being curved to be seated over a protuberance at a head of the first metacarpal and a shaft extending from the head, the shaft including an elongated fixation element hole elongated in a direction parallel to a longitudinal axis of the bone plate.

BRIEF DESCRIPTION OF THE DRAWINGS

Several embodiments of the invention will be described in the following by way of example and with reference to the accompanying drawings in which.

DETAILED DESCRIPTION

Figure 1:
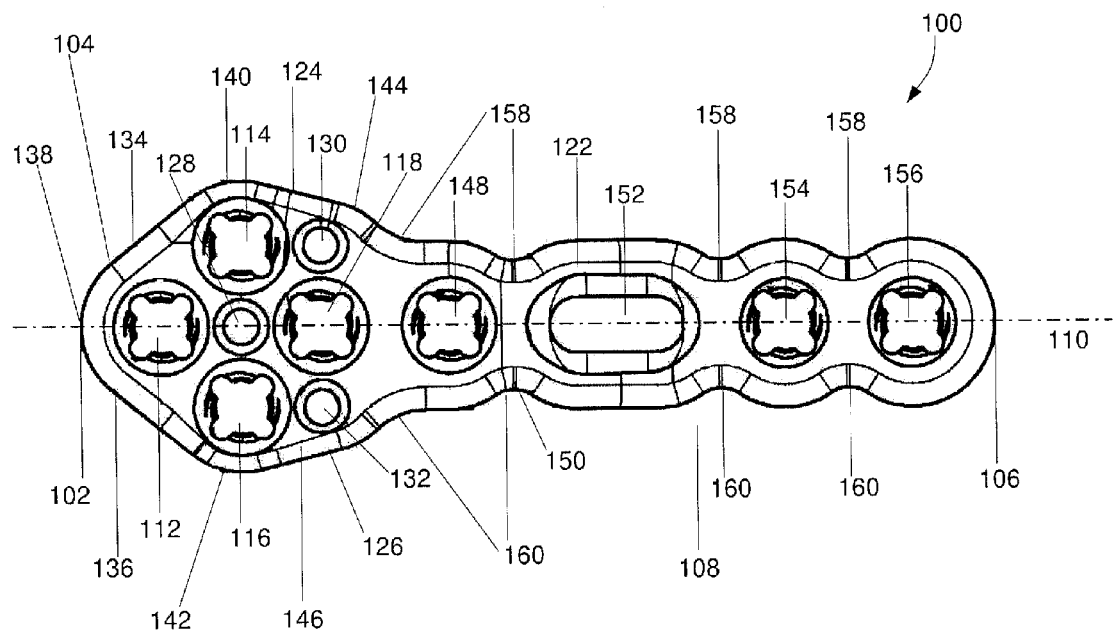
FIG. 1 shows a top view of a bone fixation plate according to an exemplary embodiment of the invention.

The exemplary embodiments may be further understood with reference to the following description and the appended drawings, wherein like elements are referred to with the same reference numerals. The exemplary embodiments relate to apparatus and methods for the treatment of fractures and, in particular, to devices for fixing fractures of the first metacarpal. More specifically, the exemplary bone fixation plates may be used for the fixation of extra-articular, intra-articular and epibasal fractures of the first metacarpal. Exemplary embodiments describe a bone fixation plate having a head at a first end with an elongated shaft extending therefrom to a second end. The head of the exemplary bone plate is generally rhombus or diamond shaped with first, second, third and fourth side walls angled relative to one another to form a diamond-shaped outer profile. The head of this exemplary plate includes first, second, third and fourth variable angle fixation holes adjacent to corners of the diamond enclosed by the head. The head also includes a plurality of guidewire holes to aid in positioning of the bone plate over the bone. Still further, the head comprises a fifth variable angle fixation hole adjacent to a neck region. The shaft includes an elongated hole extending along a hole axis parallel to a longitudinal axis of the bone plate. As will be described in greater detail later on, the elongated hole aids in positioning the bone plate over a target portion of the bone. The shaft further comprises sixth and seventh variable angle locking holes on either side of the elongated hole, in alignment with the longitudinal axis of the bone plate, as will also be described in greater detail later on. A plurality of notches is distributed over the outer border of the bone plate. A bone contacting surface of the head has a curvature selected to conform to a curvature of a dorsal wall of the first metacarpal base to ensure flush seating of the plate thereover. Specifically, a curvature of the bone contacting surface is formed to permit seating of the bone plate over a protuberance of the first metacarpal, as those skill in the art will understand. In contrast, present systems for the fixation of the first metacarpals are formed with T-shaped profiles explicitly configured to eliminate any contact with the protuberance of the bone. The exemplary diamond shape of the bone plate according to the invention has a smaller contacting surface area when compared to conventional T-shaped bone plates, thereby reducing tissue irritation and post-implantation discomfort. Furthermore, the exemplary diamond shape is suited to a greater portion of the population, thereby reducing the need for hospitals to carry a large variety of bone plates to suit different patients. As will be described in greater detail later on, the exemplary shape, size and contour of the exemplary plate permits the bone plate to be positioned along a dorsal wall of the first metacarpal.

Figure 2:
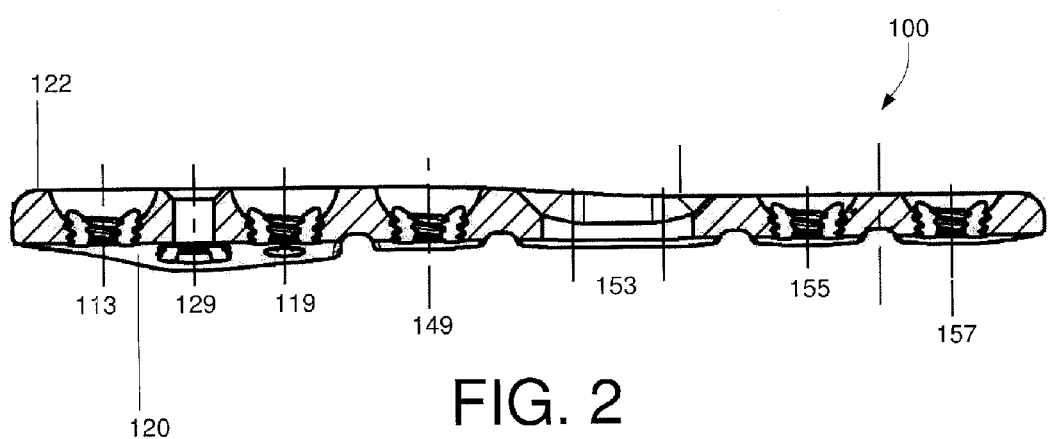
FIG. 2 shows a side view of the bone fixation plate of FIG. 1.

As shown in FIGS. 1-2, an exemplary bone plate 100 has a head 104 at a first end 102 thereof and a shaft extending therefrom along a central longitudinal axis 110 to a second end 106. The head 102 is substantially rhombus or diamond shaped and includes first, second, third and fourth variable angle plate holes 112, 114, 116, 118 extending therethrough from a bone contacting surface 120 to an upper surface 122. Trajectories for the plate hole axes (113 and 119 depicted in FIG. 2) are selected to capture common fracture patterns while avoiding the articular surfaces of the bone and minimizing interference with adjacent collateral ligaments. For example, computed tomography scan data may be used to select trajectories for these hole axes 113, 119 optimized to suit the most commonly encountered anatomy of the target portion of bone while the variable angle feature of the plate holes 112, 114, 116, 118 permits a surgeon to vary the angle at which screws are inserted through these holes (relative to the hole axes) to optimize these trajectories to suit the anatomy of a particular patient. The first and fourth variable angle plate holes 112, 118 are aligned and centered about along the central longitudinal axis 110. Second and third variable angle plate holes 114, 116 are located on first and second sides, respectively, of the axis 110 toward first and second side walls 124, 126 and are equidistant from the axis 110.

The head 104 also comprises first, second and third guidewire holes 128, 130, 132, respectively, extending therethrough and sized to receive a guidewire (e.g., a Kirschner wire). Each of the guidewire holes 128, 130, 132 is non-threaded and includes a smooth inner surface formed to slidingly receive the guidewire. In an exemplary embodiment, each of the guidewire holes 128, 130, 132 has a diameter of 1.0 mm to receive a guidewire (not shown) having a diameter of 1.0 mm or smaller therethrough. The first guidewire hole 128 is positioned between the variable angle plate holes 112, 114, 116, 118 while the second and third guidewire holes 130, 132 are located on first and second sides of the fourth variable angle plate hole 118. In one embodiment, the guidewire holes 128, 130, 132 extend through the bone plate orthogonal to the bone contacting surface 120 to the top surface 122, as shown in the partial cross-sectional view of FIG. 2 depicting a trajectory 129 of the first guidewire hole 128. It will be understood by those of skill in the art that the guidewire holes 128, 130, 132 may be used by a surgeon or other user to provide preliminary fixation of the plate 100 to a bone. The guidewire holes 128, 130, 132 may also be used to provide a general idea of the screw trajectories in the head 104 of the plate 100. Although the exemplary embodiments show and describe three guidewire holes 128, 130, 132, it will be understood by those of skill in the art that the plate 100 may include any number of guidewire holes.

The diamond-shaped configuration of the head 104 is selected to minimize a profile of the bone plate 100 without compromising the structural integrity thereof. Specifically, first and second walls 134, 136 of the head converge to a first corner 138 at a proximalmost end 102 of the bone plate 100. Thus, the diameter of the head 104 is smallest at the proximalmost end 102, increasing to a maximum diameter at a second and third corners 140, 142. An angle of the first and second walls 134, 136 relative to the axis 110 may be approximately 40 degrees. Third and fourth walls 144, 146 extend from the second and third corners 140, 142 toward the shaft 108. An angle of the third and fourth walls 144, 146 relative to the axis 110 may be approximately 20 degrees. It will be understood by those of skill in the art that angles between the walls 134, 136, 144, 146 and the axis 110 may vary so long as the head 104 is sized and shaped to be positioned along a head portion of the bone. As those of skill in the art will understand, the reduced diameter at the first corner 122 permits the bone plate 100 to be seated closer to, or on a head of the target bone than would be possible with a bone plate with a larger profile. Furthermore the curvature of the bone-contacting surface 120 is selected to conform to the curvature of the dorsal aspect of the first metacarpal to ensure a flush fit therewith. In one embodiment, the bone-contacting surface 120 of the head 104 includes curvatures of varying radii. A predetermined length of the head 104 at the second and third corners 140, 142 may be curved downward toward the bone toward a palmar surface of the bone when implanted in a desired configuration. This downward curvature aids in reduction of the fracture.

The head 104 also includes a fifth variable angle plate hole 148 adjacent to a reduced diameter neck 150 connecting the head 104 to the shaft 108. A trajectory of a hole axis 149 of the fifth plate hole 148 is orthogonal to the bone contacting surface 120 and extends to the upper surface 122 while the variable angle feature of the plate hole 148 permits a surgeon to vary the angle at which a screw is inserted therethrough. The fifth plate hole 148 is centered about along the central longitudinal axis 110.

The shaft 108 extends distally from the neck 105 to the distal end 106 and includes an elongated hole 152 elongated in a direction parallel to the longitudinal axis 110. An axial length of the elongated hole 152 is at least larger than a diameter of the first through fifth plate holes 112, 114, 116, 118, 148 while a width of the elongated hole 152 may be equivalent to the diameter of the first through fifth plate holes 112, 114, 116, 118, 148. In a preferred embodiment, the first through fifth plate holes 112, 114, 116, 118, 148 are 1.5 or 2.0 mm variable angle holes. However, it is noted that any other diameter of the holes may be used without deviating from the scope of the invention to conform to the requirements of a particular procedure. As will be described in greater detail below with respect to the exemplary method, the elongated hole 152 permits a surgeon or other user to slide the bone plate 100 over the bone within a predetermined range (i.e., corresponding to a length of the elongated hole 152) prior to locking the bone plate 100 in place but after the placement of a screw therein. Specifically, the elongated hole 152 allows axial movement along the longitudinal axis 110 while also permitting rotation of the bone plate 100 therearound, as will also be described in greater detail later. The exemplary elongated plate hole 152 extends orthogonally through the bone plate from the bone contacting surface 120 to the upper surface 122 along a trajectory 153.

The shaft 108 further comprises sixth and seventh variable angle plate holes 154, 156 centered about the axis 110, trajectories 155, 157 thereof extending orthogonally through the bone plate 100 from the bone contacting surface 120 to the upper surface 122 while the variable angle features of the plate hole 154, 156 permit a surgeon to vary the angle at which a screw is inserted therethrough. Thus, the trajectories 155, 157 may assume any path selected to lockingly engage the bone without extending through an opposing cortical surface thereof.

The bone-contacting surface 120 of the shaft 108 is curved along the longitudinal axis 110 to conform to the substantially cylindrical shape of the target portion of the bone over which the shaft 108 will be seated. In one embodiment, the length of the shaft 108 may include a single uniform curvature. In another embodiment, the bone contacting surface 122 of the shaft 108 may have a complex shape formed of a plurality of curves selected to ensure that the shaft 108 is seated flush over the bone.

The bone plate 100 also includes a plurality of first webbed portions 158 extending along the first side wall 124 between each of the holes 118, 148, 152, 154, 156 and a plurality of second webbed portions 160 extending along the second side wall 126 between each of the holes 118, 148, 152, 154, 156. The first and second webbed portions 158, 160 are formed as notches extending into the width of the bone plate 100 reducing a profile thereof while maintaining the structural integrity of the bone plate 100. The first and second webbed portions 158, 160 are sized to maintain a minimum desired clearance remains around the boundary of each of the plate holes of the bone plate 100. An outer periphery of the bone plate 100 may include a rounded taper to further reduce the profile as would be understood by those skilled in the art.

In accordance with an exemplary method according to the invention, the bone plate 100 is positioned over a target portion of a bone 10. Specifically, the bone plate 100 is positioned over a dorsal surface of a first metacarpal. The surgeon or other user approximates the desired position of the bone plate 100 over the bone and inserts a cortex screw (not shown) through the elongated hole 152 and into the bone to a first depth sufficient to hold the bone plate 100 over the bone while still permitting movement of the bone plate 100 relative to the bone. The bone plate 100 is then slid axially along the length of the elongated hole 151 and/or rotated about the cortex screw (not shown) until a final target position has been achieved. The exemplary system and method according to the invention bypasses the need for pre-drilling holes in the bone. Rather, once the target position has been achieved, bore holes are drilled through any of the variable angle plate holes into the bone. In contrast, present bone fixation systems require the insertion of a guidewire into the bone prior to the placement of the bone plate over the bone, thus requiring the selection of a final position of the bone plate 100 prior to the placement of the bone plate over the bone. This method may lead to reduced accuracy in placement, especially in the fixation of the metacarpal bone where even the smallest deviation, (e.g., in millimeters) from a correct position may lead to less than optimum fixation. The exemplary bone plate 100, on the other hand, permits adjustment of the position of the bone plate 100 even after the bone plate 100 has been initially secured to the bone, thereby ensuring that the final position of the bone plate 100 captures all fragments of the bone while avoiding interference with ligaments, tendons or other tissue.

Once the bone plate 100 has been moved to the target position, a guidewire (not shown) is optionally inserted into any of the guidewire holes 128, 130, 132. The guidewire (not shown) serves to retain the bone plate 100 in the target configuration while bone screws are inserted into plate holes thereof. In another embodiment, this step may be omitted. A bone screw (not shown) is then inserted into the first plate hole 112. Bone screws (not shown) may then be inserted into any of the remaining variable angle plate holes 114, 116, 118, 148, 154, 156 depending on the fracture pattern. The bone screw inserted into the elongated plate hole 152 may be tightened to firmly engage the bone plate 100.

It will be appreciated by those skilled in the art that various modifications and alterations of the disclosed embodiments may be made without departing from the broad scope of the invention. Some of these have been discussed above and others will be apparent to those skilled in the art.

What is claimed is:

1. A bone plate sized and shaped for fixation to a phalangeal bone, comprising:
a head extending from a first end to a second end and having first, second third and fourth fixation element holes extending therethrough and arranged in a diamond configuration on the head, an outer wall of the head having a diamond shape corresponding to the diamond configuration, a bone contacting surface of the head being contoured to conform to the anatomy of a dorsal surface of a first metacarpal, the contour being curved to be seated over a protuberance at a head of the first metacarpal; and a shaft extending from the head, the shaft including an elongated fixation element hole elongated in a direction parallel to a longitudinal axis of the bone plate, wherein the head includes a guidewire hole extending therethrough.

2. The bone plate of claim 1, wherein an axial length of the head along the longitudinal axis is greater than a width of the head.

3. The bone plate of claim 2, wherein the elongated fixation element hole is centered about the longitudinal axis.

4. The bone plate of claim 1, wherein the second and third plate holes are aligned along an axis extending orthogonal to the longitudinal axis at a location having a maximum width of the head.

5. The bone plate of claim 1, wherein the bone plate is symmetric about the longitudinal axis.

6. The bone plate of claim 1, further comprising a reduced diameter neck extending between the head and the shaft.

7. The bone plate of claim 6, wherein the shaft further comprises fifth and sixth fixation element holes extending along the longitudinal axis.

8. The bone plate of claim 6, further comprising a plurality of notches formed in first and second side walls of the bone plate, the plurality of notches defining reduced width regions of the bone plate.

9. The bone plate of claim 6, further comprising a tapered region extending around a periphery of the bone plate to reduce a profile thereof.

* * * * *

UNITED STATES PATENT AND TRADEMARK OFFICE
CERTIFICATE OF CORRECTION

| | |
|---|---|
| PATENT NO. | : 9,801,670 B2 |
| APPLICATION NO. | : 14/320542 |
| DATED | : October 31, 2017 |
| INVENTOR(S) | : Hashmi et al. |

It is certified that error appears in the above-identified patent and that said Letters Patent is hereby corrected as shown below:

Claim 7, Column 6, Line 25:
"7. The bone plate of claim 6, wherein the shaft further" should read "7. The bone plate of claim 1, wherein the shaft further".

Claim 8, Column 6, Line 28:
"8. The bone plate of claim 6, further comprising a" should read "8. The bone plate of claim 1, further comprising a".

Claim 9, Column 6, Line 32:
"9. The bone plate of claim 6, further comprising a tapered" should read "9. The bone plate of claim 1, further comprising a tapered".

Signed and Sealed this
Tenth Day of July, 2018

Andrei Iancu
*Director of the United States Patent and Trademark Office*